United States Patent [19]
Lesinski

[11] Patent Number: 4,655,776
[45] Date of Patent: Apr. 7, 1987

[54] PROSTHESES FOR OSSICULAR RECONSTRUCTION

[75] Inventor: S. George Lesinski, Cincinnati, Ohio

[73] Assignee: Oto Enterprises, Inc., Cincinnati, Ohio

[21] Appl. No.: 570,089

[22] Filed: Jan. 12, 1984

[51] Int. Cl.⁴ .............................................. A61F 2/18
[52] U.S. Cl. .................................................... 623/10
[58] Field of Search .............. 623/10; 128/92 C, 92 G

[56] References Cited

U.S. PATENT DOCUMENTS

| | | | |
|---|---|---|---|
| 3,473,170 | 11/1969 | Hasse et al. | 623/10 |
| 4,130,905 | 12/1978 | Mercandino | 623/10 |
| 4,169,292 | 10/1979 | Grote | 623/10 |
| 4,215,438 | 8/1980 | Pappas | 623/10 |
| 4,281,419 | 8/1981 | Treace | 633/10 |

Primary Examiner—Richard J. Apley
Assistant Examiner—David J. Isabella
Attorney, Agent, or Firm—Frost & Jacobs

[57] ABSTRACT

Prostheses for reconstruction of the ossicles of the middle ear, comprising an elongated lever member replacing the incus and providing a mechanical advantage at least as great as that of natural middle ear ossicles, means for attachment thereof to the stapes if intact, or a synthetic stapes when the natural stapes is absent. A prosthesis for replacement only of the stapes is also disclosed. A method of stabilizing reconstructive prostheses for short-term and long-term hearing restoration is provided, comprising laser welding of prostheses in selected positions and placing porous surfaces of prostheses in contact with host bone whereby to promote bone ingrowth.

10 Claims, 12 Drawing Figures

PROSTHESES FOR OSSICULAR RECONSTRUCTION

BACKGROUND OF THE INVENTION

This invention relates to prostheses for surgical reconstruction of the auditory ossicles of the middle ear which provide mechanical lever advantage to the transmission of sound pressure into the inner ear. This provides repair of conductive hearing loss with permanent restoration of normal hearing, with both short-term and long-term stability of the prosthesis after implanting, and avoids the danger of extrusion through the tympanic membrane (ear drum) as well as excessive pressure on the oval window of the inner ear.

The prostheses of the invention are fabricated from materials which are biologically inert, i.e., no resorption and no host reaction such as inflammation, foreign body reaction or scar tissue.

The prior art has utilized bone transplants for replacement of portions of the ossicular chain in the middle ear. Although this is considered the most reliable procedure at present, it suffers from serious disadvantages, viz., loss of the middle ear mechanical amplification of sound and therefore less than normal hearing restoration, instability of reconstruction resulting in progressive worsening of hearing as the prosthesis migrates, resorption of bone, and excessive pressure on the oval window causing dizziness.

Various synthetic polymeric and metallic prostheses have been used in the prior art. These have generally met with long-term failure (2-3 years after implantation) with consequent loss of hearing because of instability, extrusion through the tympanic membrane, or biodegradability.

Short-term hearing restoration was reported for TORP and PORP synthetic ossicles, but only 15%-25% of these implants maintained satisfactory hearing five years postoperatively.

U.S. Pat. No. 3,710,399 discloses a prosthesis for surgically replacing the malleus, incus and stapes of the middle ear, comprising two biochemically inert wire struts mechanically held in parallel partly overlapping relation, with one end to be surgically attached to the tympanic membrane and the other end to be attached to the oval window, the struts being magnetically coupled to transmit sound oscillations. This prosthesis to does not have a mechanical lever advantage to amplify sound and would tend to be unstable, to extrude through the tympanic membrane and to place excessive pressure on the oval window.

U.S. Pat. No. 4,130,905 discloses an artificial malleus columella for the human ear comprising an elongated member angled downwardly to provide first and second linear portions, a stem extending from the underside of the first linear portion to contact the stapes when installed, and a clamp located on the external surface of the angle and extending over the second linear portion to engage the bridge of the ear. This prosthesis has not been used successfully because it does not amplify sound, is cumbersome to use, and would tend to be unstable.

U.S. Pat. No. 4,215,438 discloses a prosthesis intended to connect the incus and stapes, comprising a goblet-shaped member having an open cup-like end adapted to receive the capitulum of the stapes, and an integral stem adapted to be inserted in a hole drilled in the incus. Preferably the prosthesis is of stainless steel. It is apparent from the above summary of the disclosure that this prosthesis has utility only as a replacement for the damaged lenticular proces of the incus. It is surgically extremely difficult to drill a hole into the incus without disruption of the incudo-mallear joint and thus the integrity of the ossicular chain.

Despite the extensive studies devoted to auditory ossicular reconstruction and the numerous prostheses which have been proposed and tested, there is not now an available prosthesis which permits single-stage ossicular reconstruction for all combinations of middle ear ossicle damage and which provides in combination a lever advantage equal to or greater than natural hearing, stable short-term connection between the malleus and the inner ear preventing loss of vibrational energy and rotation of the prosthesis, avoidance of extrusion through the tympanic membrane, long-term stability due to ingrowth of host bone into the porous surfaces of the prosthesis, biologically inert materials, a single size prosthesis for replacement of the incus adaptable to any size human ear, stability of connections to existing ossicles by laser welding or bonding adhesives, and reduction of pressure against the oval window eliminating dizziness and the risk of inner ear fluid leak with consequent infection.

SUMMARY OF THE INVENTION

It is a primary object of the invention to provide prostheses which will achieve the advantages and desirable features set forth above. More specifically, the present invention incorporates the following novel features:

1. a mechanical lever advantage to restore hearing to 100% of normal rather than the presently otainable 85% of normal;
2. the use of lasers to weld and shape prostheses of the invention to custom fit them in the ear;
3. the custom fitting of prostheses of the invention to promote short-term stability and thus consistent long-term hearing results;
4. a porous connection to the stapes bone and to the malleus bone encouraging host bony ingrowth, thus obtaining long-term connections without erosion of the bone;
5. elimination of the risk of extrusion through the typmanic membrane, in direct contrast to prior art prostheses;
6. ability to reduce the weight or pressure exerted on the oval window and thus to eliminate the risk of perilymph leak and dizzines, thereby allowing single-stage surgical repair instead of two operations several months apart;
7. the adaptability of prostheses of the invention to reconstruct all combinations of ossicular problems in the middle ear whether related to the malleus, incus and/or stapes.

The invention is designed to repair all possible combinations of ossicular damage in the middle ear.

When the incus is missing or deteriorated (the most common clinical problem) but the malleus and stapes are intact, a prosthesis in one embodiment of the invention is attached to the malleus, and a porous cup-shaped prosthesis is placed on the head of the stapes and welded to the adjustable prosthesis. When both the incus and stapes are missing, a stapes prosthesis is laser welded to the prosthesis of the first embodiment. Finally, when all three ossicles (malleus, incus and stapes)

are absent, the prosthesis of the first embodiment is attached to a homograft malleus and tympanic membrane, and the appropriate stapes prosthesis welded to the prosthesis of the first embodiment.

In another embodiment a prosthesis is provided for use in cases where the malleus and incus are intact and the stapes is absent or deteriorated.

According to the invention there is provided a prosthesis for attachment to a host malleus or to a homograft malleus and tympanic membrane when the host malleus is absent, said prosthesis comprising an elongated lever member replacing the natural incus which collects sound from the tympanic membrane and transmits said sound to the oval window of the inner ear with a mechanical advantage at least as great as that of the natural middle ear ossicles.

When the stapes is intact means is provided for an adjustable connection from the elongated lever member to the stapes comprising a U-shaped member adapted to be crimped around the elongated lever member and fixedly welded thereto at a selected position, and a dependent inverted cup-like member having a concave porous inner surface for ingrowth of bone adapted to engage the capitulum of the stapes.

When the incus and stapes are absent the prosthesis defined above is supplemented by a synthetic stapes comprising a smooth surface foot plate adapted to contact the oval window without fixation to its surrounding bony edges, an inverted U-shaped member the legs of which are secured to the foot plate, and a malleable band secured to the top of the U-shaped member and projecting away from the foot plate. The malleable band will be attached by mechanically crimping it around the elongated lever member defined above and then laser welded or bonded with a chemical adhesive.

According to the invention there is further provided a prosthesis for ossicular reconstruction in the middle ear when the malleus and incus are intact and the stapes is absent, comprising a smooth-surfaced foot plate adapted to contact the oval window in the middle ear with no fixation to surrounding bony edges, and an inverted U-shaped member the legs of which are secured to said foot plate, a cup-like member secured to the top of said U-shaped member and projecting away from said foot plate, said cup-like member having a concave porous inner surface adpated for ingrowth of bone thereinto, said concave inner surface being configured to surround the lenticular process of the incus remote from the malleus, a concave arm secured to said cup-like member and projecting superiorly under the long process of the host incus terminating in a malleable U-shaped band which will be "crimped" to encircle the long process of the incus and then be welded by laser. The prosthesis is designed to eliminate the risk of erosion of the incus with resultant loss of hearing. All the above porous surfaces will have a porosity of about 50-150 microns to encourage ingrowth of bone between the incus and the prosthesis for long-term stability.

A method of stabilizing middle ear reconstructive prostheses in accordance with the invention comprises securing said prostheses in selected positions by at least one of laser welding and bonding with a chemical adhesive for immediate stability, and providing porous surfaces on those portions of said prostheses which contact host bone, whereby to promote long-term stability between host bone and prostheses by encouraging ingrowth of host bone into said porous sufaces. As indicated above the porosity is on the order of about 50 to about 150 microns.

DETAILED DESCRIPTION

Figure 1:
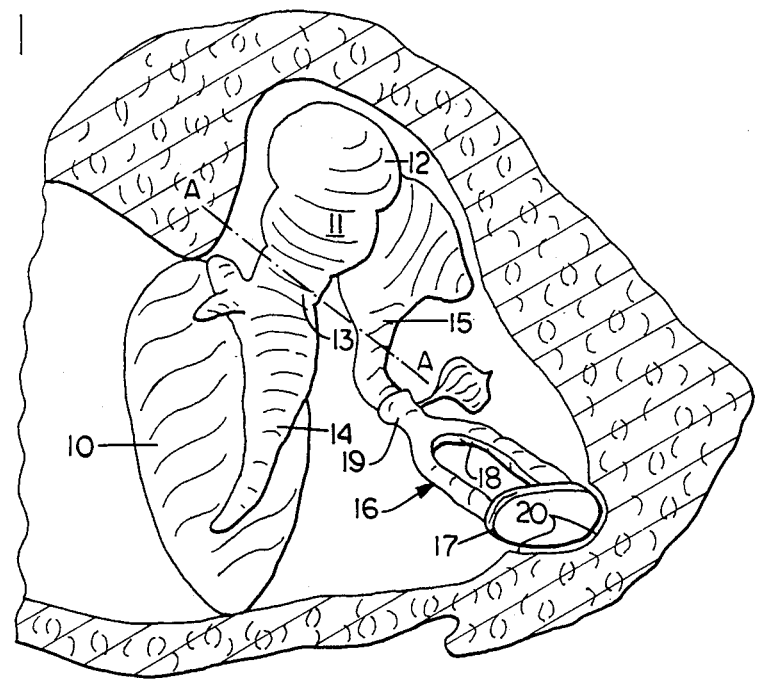
FIG. 1 is a diagrammatic illustration of the auditory ossicles of the human ear in the normal condition.

By way of background, and referring to FIG. 1 of the drawings, the anatomy of that part of the human ear to which the present invention pertains includes the tympanic membrane (eardrum) indicated at 10, the malleus indicated generally at 11, having a relatively massive head 12, narrow neck 13 and manubrium indicated at 14 which is attached to the tympanic membrane. The incus indicated at 15 has a synovial joint with the malleus head, a long process terminating in a lenticular process which articulates with the stapes indicated generally at 16. The stapes (stirrup) includes a foot plate 17, two arches 18 attached to the foot plate and the capitulum 19 articulating with the lenticular process of the incus. Foot plate 17 is held in the oval window 20 of the cochlea (entrance into the inner ear) by an annular ligament (not shown). The cochlea (not shown) is filled with fluid perilymph and endolymph.

The function of the middle ear is to collect sound waves from the air, amplify them and then transmit the sound pressure vibrations into the fluid of the inner ear. Because of impedance (resistance) mismatching between air molecules and the more dense inner ear fluid molecules of the perilymph, the receiving sound energy is amplified greatly before it enters the oval window. This is accomplished by three mechanisms: (a) the cantilever effect of the concave eardrum as its collecting lever of the manubrium of the malleus; (b) the mechanical lever action of the ossicular chain of the malleus, incus, stapes; and (c) the large collection area of the tympanic membrane compared with the small area of the oval window.

The ossicles of the middle ear described above have a center of gravity and an axis of rotation (fulcrum) about which the ossicles vibrate when transmitting sound from the tympanic membrane. Supporting ligaments (not shown) hold the ossicles in place at this axis of rotation (fulcrum of the lever), but do not participate in transmission of sound. In effect, the ossicular chain vibrates freely in the middle ear and provides a mechanical advantage of 1.3 or 1.4.

The mass of the malleus head and incus are such that the center of gravity and axis of rotation are indicated by the broken line A—A in FIG. 1, which passes through the neck of the malleus and the short process of the incus.

A more detailed explanation of the functioning of the middle ear can be found in "Experiments in Hearing" by G. von Bekesy, McGraw-Hill Co., 1960, pages 11–12 and 95–104, and in J. Tonndorf et al, *Ann Otol Rhinol Laryngol*, 79:743-753 (1970).

Von Bekesy and Tonndorf have studied the transformer function (amplification) of the entire middle ear mechanism. The cantilever effect is reported to provide a 2 power amplification, the ossicular chain 1.4 power amplification (1.3 according to von Bekesy), and the effective area ratio of the tympanic membrane relative to the oval window a 34.6 power magnification. The total ratio of amplification of sound pressure from the tympanic membrane is thus 96.9 (2×1.4×34.6), which is equivalent to 39.7 decibels.

It has been determined clinically that patients lacking a tympanic membrane or having a disrupted ossicular chain suffer a 40 to 50 decibel hearing loss, thus confirming the accuracy of the above laboratory studies.

Reconstruction in accordance with the present state of the art provides only about a 20 to 25 decibel level of hearing, because of limitation on the cantilever effect of the tympanic membrane and its connection to the manubrium of the malleus, and loss of the lever mechanical advantage of the ossicular chain.

In contrast to this the prostheses of the present invention not only restore the natural lever advantage of the ossicular chain but actually increase the mechanical advantage to 2:1 to 3:1. At the same time the cantilever effect is retained along with the 34.6 power amplification of the area ratio of the tympanic membrane to the oval window. There is thus provided a total ratio of amplification ranging from about 138 (2.0×2.0×34.6) to about 208 (2.0×3.0×34.6).

Figure 2:
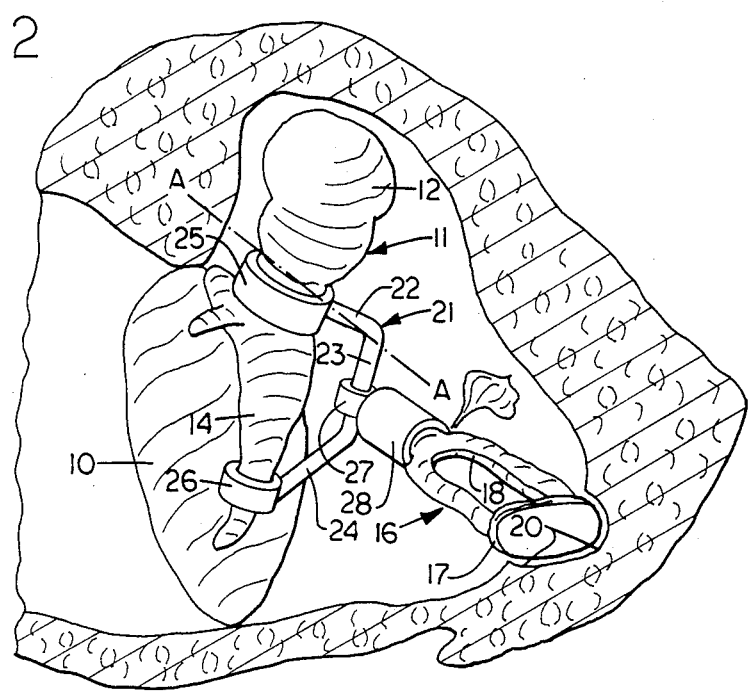
FIG. 2 is a diagrammatic illustration of a prosthesis of the invention which has been surgically installed as a replacement for the incus.
Figure 3:
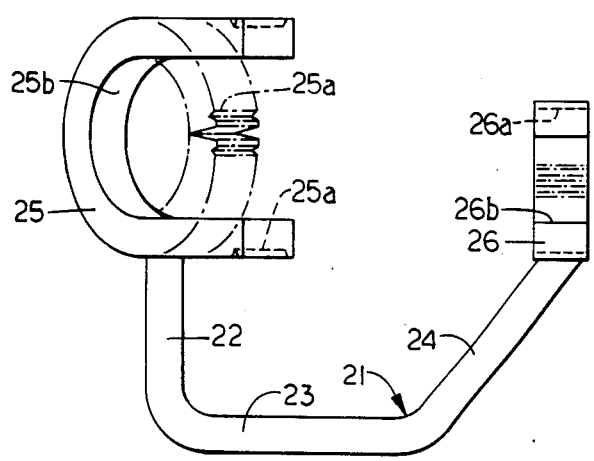
FIG. 3 is an orthographic drawing of the prosthesis shown in FIG. 2.
Figure 4:
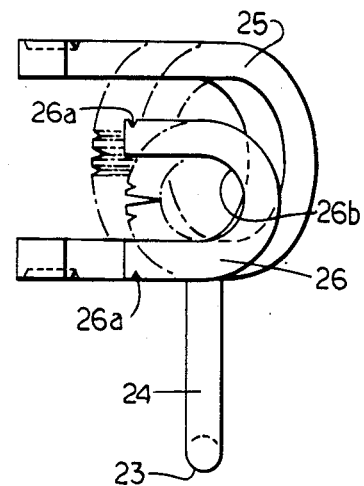
FIG. 4 is a front view of the prosthesis of FIG. 3.

Surgical replacement or reconstruction of the incus, in accordance with the present invention, is effected by means of the prosthesis illustrated in FIGS. 2–4 of the drawings. Referring to FIGS. 3 and 4, the prosthesis, indicated generally at 21, comprises an elongated lever member having a first linear portion 22, a second linear portion 23 substantially at right angles to portion 22, and a third linear portion 24 extending at an obtuse angle to the second linear portion at the end of second linear portion 23 remote from the first portion 22. A first U-shaped band indicated at 25 is secured to the free end of first linear portion 22. A second U-shaped band indicated at 26 is secured to the free end of the third linear portion 24. Bands 25 and 26 are in non-parallel planes. When installed surgically the first U-shaped band 25 is deformed by a crimping tool into a cylindrical configuration encircling the malleus neck 13 at the axis of rotation of the ossicles, as shown in FIG. 2. The cylindrical configuration is shown in broken lines in FIGS. 3 and 4. Preferably the U-shaped band 25 is provided with notches 25a on each side adjacent to the upper ends of the legs for engagement by a crimping tool. Once crimped, the band will be welded closed with a laser beam or bonded with chemical adhesive.

Similarly, the second U-shaped band 26 is malleable and will encircle the power portion of the manubrium 14. This is accomplished by elevating a small strip of periosteum and tympanic membrane off the malleus adjacent the umbo thereof and sliding the band under the tympanic membrane around the malleus, then crimping the band and finally laser welding. The outside surfaces of the band 26 will preferably be notched as shown in 26a, in the same manner as band 25.

As will be evident from FIG. 2, when the bands 25 and 26 are securely attached to the malleus, the eardrum vibrations will now be transmitted from the malleus to the prosthesis 21. Arm 22 is the axis or fulcrum of the ossicular chain and the band 26 remote therefrom transmits the maximum movement of the malleus. Because the length of second linear portion 23 is one-half the distance between the bands 25 and 26, a mechanical advantage is accomplished with a magnification of power increased 2 times. As will be explained later this may be increased to about 3:1.

Figure 5:
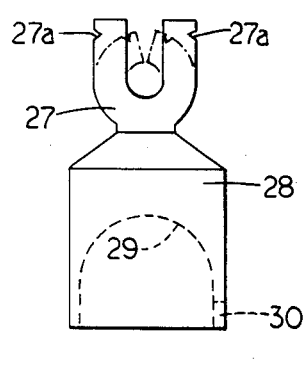
FIG. 5 is an orthographic drawing of means engaging the stapes.
Figure 6:
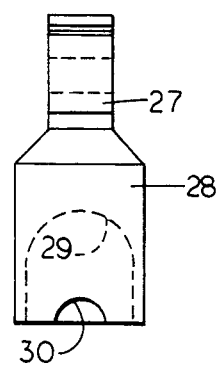
FIG. 6 is a front plan view of the means of FIG. 5.

When the stapes is intact means engaging the stapes comprising an inverted cup-like prosthesis 28 shown in FIGS. 5 and 6 will be placed on the stapes capitulum. A U-shaped member 27 projecting from prosthesis 28 is crimped to the portion 23 and laser welded for stability. The inner surface 29 of prosthesis 28 is porous, the pore size being 50 to 150 microns, to establish bone growth from the capitulum to the prosthesis. The position at which member 27 is attached to linear portion 23 can change the effective length thereof, resulting in a mechanical advantage up to 3:1.

The inner surfaces 25b and 26b of bands 25 and 26, respectively, and the inner surface 29 of member 28 are all fabricated with a porous inner surface to encourage ingrowth of bone. This may be affected in a number of ways known in the art. The prostheses of FIGS. 3–6 are fabricated of material which is biologically inert, i.e., no resorption and no host reaction such as inflammation, foreign body reaction or scar tissue. Suitable materials include platinum, stainless steel, tantalum, titanium, a wide number of both bioactive and inert ceramics, polyethylene, polypropylene, polytetrafluorethylene (teflon) and other suitable material. Etching techniques can be used to impart porosity to the surfaces of metal such as stainless steel, tantalum and titanium. Alternatively, mechanical roughening can be used, particularly in the case of platinum. The technique also involves application of a porous ceramic coating to metallic surfaces or developing porous ceramic prostheses.

It has been found that about 50 to about 150 microns pore size provides maximum osteoblastic acivity resulting in a secure bond between the prosthesis and the host bone.

Figure 7:
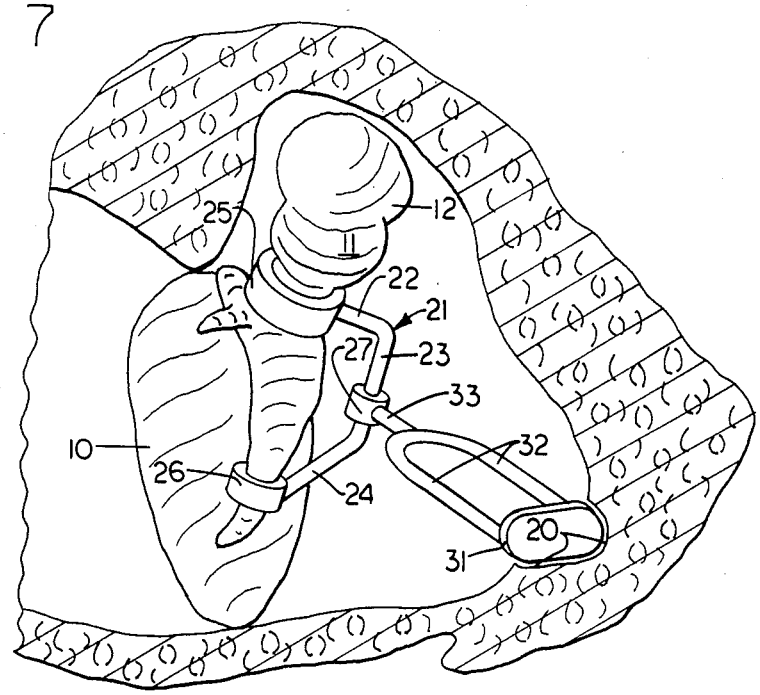
FIG. 7 is a diagrammatic illustration similar to FIG. 2 further including a synthetic stapes.
Figure 8:
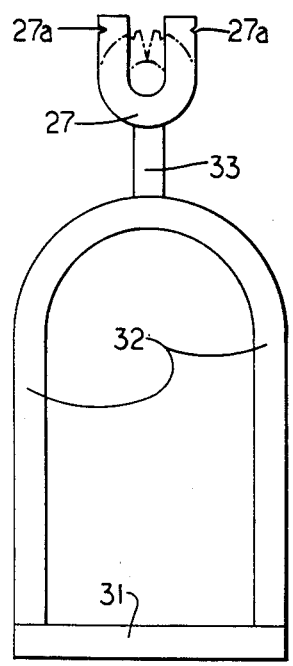
FIG. 8 is an orthographic drawing of the synthetic stapes shown in FIG. 7.
Figure 9:
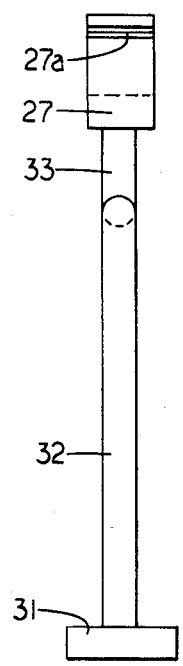
FIG. 9 is a side view of the synthetic stapes of FIG. 8.

A variety of porous ceramic materials are suitable, including calcium aluminate, titanium dioxide, cerosium (a ceramic-epoxy resin composite), and aluminum oxide. Reference may be made to Hulbert et al, *Journal Biomedical Materials Research*. Vol. 15 (1981) pp 73–82.

Where deterioration or loss of the stapes is associated with loss of the incus, the prosthesis shown in FIGS. 2–4 is combined with a synthetic stapes as shown in FIGS. 7, 8 and 9. Referring to FIGS. 8 and 9, the synthetic stapes comprises a foot plate 31 having a smoothly polished inert outer surface which will resist fixation to the bony edges surrounding the oval window. The stapes further comprises an inverted U-shaped member 32 the legs of which are secured to the foot plate 31, and rod-like element 33 terminating in a malleable band 27. This malleable band 27 attaches to the second linear portion 23 of the first prosthesis 21 in the manner described above. FIG. 7 shows the arrangement of the synthetic stapes when surgically installed along with a prosthesis 21.

Preferably the smoothly polished foot plate 31 is fabricated from teflon or non-porous ceramic, while the inverted U-shaped member 32 and rod-like element 33 are preferably fabricated from platinum, stainless steel, tantalum, titanium, teflon, or other similar biocompatible materials. It is within the scope of this invention to use one or more of these materials or other biocompatible similar materials provided they can be suitably secured one to another by laser welding, adhesive or the like, and provided that no electro-galvanic action is set up by juxtaposition of unlike metals.

When the U-shaped bands 25, 26 and 27 are crimped into cylindrical configurations, the stability can be enhanced by laser welding of the free ends, using $CO_2$, Argon, Nd YAG or other suitable medical laser. Alternatively, bonding adhesives capable of effecting a metal-to-metal bond can be used, e.g. cyano-acrylic types being known which are effective for this purpose. The bands may simply be mechanically crimped into a cylindrical configuration although welding or adhesives as described above are preferably utilized to insure long-term stability.

Measurements conducted by applicant of various dimensions of the malleus, incus and stapes in over 50 human patients have established the variations in size and relationships. As a result, it has been determined that the prosthesis 21 can be made in a single size, and can be adapted for use in any human ear, adult or child, by only minor adjustment or bending, e.g. of the angles between linear portions 22 and 24 or the plane angles of bands 25 and 26. On the other hand, where a synthetic stapes is needed, it has been found that three different sizes will be required to accommodate differences among individual patients.

The above-described prostheses provide a lever advantage equal to or greater than that of the natural ossicular chain, thus providing full restoration of hearing where there is no damage to the auditory nerve.

The stable short-term connection between the malleus and the inner ear when the prostheses of the present invention are implanted surgically permit one-stage restoration of the ossicular chain, i.e., only a single operation is necessary. The use of the present day transplant bones or other prostheses often require two separate operations. The lateral flexibility of the prosthesis 21 in its connection with the malleus permits initial healing without loss of lever advantage, while still minimizing the pressure on the oval window. This reduces the risk of dislocating the stapes foot plate with the consequent risk of perilymph leak and attendant vertigo, nerve deafness, labyrinthitis or meningitis.

Since the prosthesis does not touch the eardrum, but is attached firmly to the malleus, there is no possibility of extrusion through the tympanic membrane.

Long-term stability is ensured because of the ingrowth of bone into the cylindrical bands 25 and 26 and the inner surface 29 of cup-shaped member 28.

Figure 10:
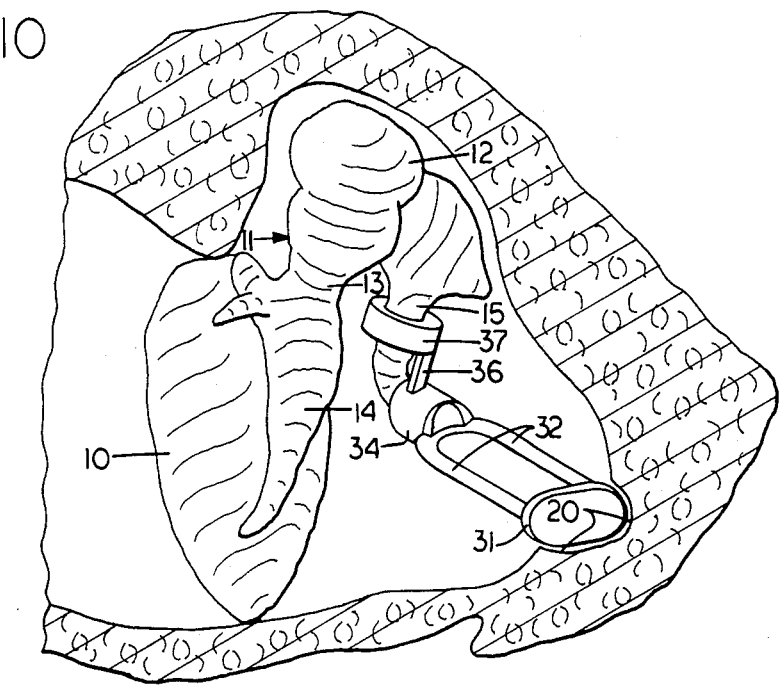
FIG. 10 is a diagrammatic illustration of a prosthesis of the invention which has been surgically installed as a replacement for the stapes when the malleus and incus are intact.
Figure 11:
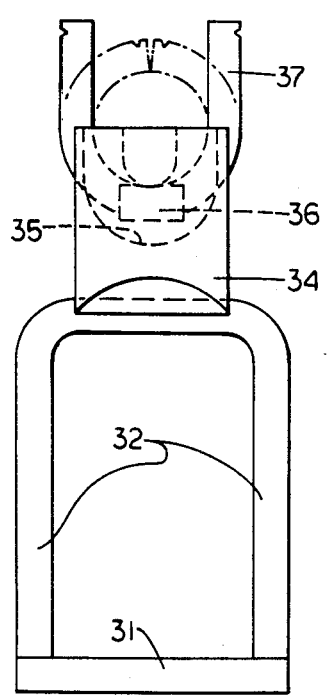
FIG. 11 is an orthographic drawing of the prosthesis shown in FIG. 10.
Figure 12:
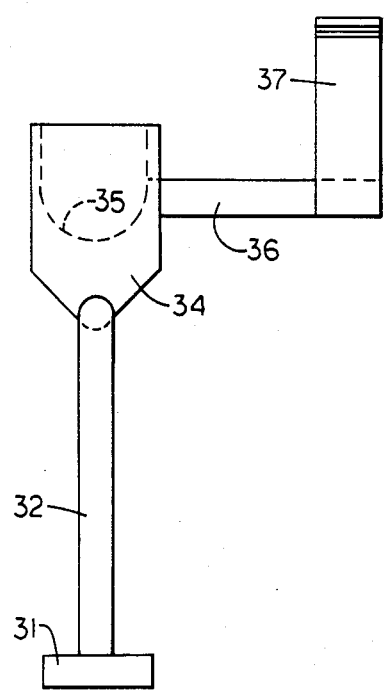
FIG. 12 is a side view of the prosthesis of FIG. 11.

Referring next to FIGS. 10, 11 and 12, there is shown a prosthesis for ossicular reconstruction when the malleus and incus are intact but the stapes is deteriorated or absent. The synthetic stapes of FIGS. 11 and 12 is similar to that of FIGS. 8 and 9 in comprising a foot plate 31' having a smoothly polished outer surface, again for the purpose of avoiding fixation to the bony edges surrounding the oval window. An inverted U-shaped member 32' is provided the legs of which are secured to the foot plate. A cup-like member 34 is secured to the top of member 32' projecting away from foot plate 31'. Member 34 has a concave porous surface 35 configured to surround the lenticular process of the incus remote from the malleus. As discussed above, porosity is imparted by etching of the metal, mechanical roughening or abrading or by a ceramic lining, and the pore sizes are preferably from about 50 to about 150 microns. The cup-like member may also contain amalgam or similar porous material which will pressure-mold to the shape of the lenticular process of the incus.

An arm indicated at 36 is secured to the cup-like member 34 and projects laterally therefrom in a direction to lie under the long process of the host incus. A U-shaped malleable band indicated at 37 is secured to the distal end of the supporting arm 36. Band 37 is deformable into a substantially cylindrical configuration which encircles the incus when surgically installed as shown in FIG. 10.

Preferably foot plate 31' is fabricated from teflon or ceramic, while the inverted U-shaped element 32', cup-like member 34, supporting arm 36 and U-shaped band 37 are fabricated from platinum, stainless steel, tantalum, titanium, ceramics or other similar biocompatible materials. The inner surface of band 37 is preferably porous, as described above, to encourage bone ingrowth.

Present techniques of stapedectomy or stapedotomy with attachment of the stapes prosthesis to the neck of the incus result in a predictable number of long-term complications all of which produce conductive deafness: (a) erosion of the neck of the incus; (b) loosening of the crimped attachment around the incus; (c) migration of the prosthesis from the center of the oval window. Besides conductive hearing loss, if the present day prosthesis migrates eccentrically in the oval window this can result in a rupture of the oval window membrane with resultant perilymph leak which causes vertigo, labyrinthitis, nerve deafness and possibly meningitis. The synthetic stapes illustrated in FIGS. 10 through 12 wil eliminate these complications.

If implanted by proper surgical technique, the prostheses of the present invention permit all patients with conductive deafness to acquire normal hearing by restoring the maximum amplification function of the middle ear, a function which is not completely restored by other prior methods now available.

I claim:

1. A prosthesis for attachment to a host malleus or to a homograft malleus and tympanic membrane when the host malleus is absent, said prosthesis comprising an elongated lever member substituted for the natural incus when the natural incus is absent which collects sound from the tympanic membrane, said elongated lever member having a first linear portion and a second linear portion joined at one end to an end of said first linear portion, said portions being substantially at right angles to one another, and a third linear portion extending at an obtuse angle to said second linear portion at the end thereof remote from said first linear portion; means for attachment of one free end of said lever member to the neck of the malleus at the axis of rotation of the malleus and means for attachment of the other free end of said lever member to the manubrium of the malleus adjacent its umbo whereby to retain the natural cantilever effect of the tympanic membrane as a collecting lever of the manubrium.

2. A prosthesis for attachment to a host malleus or to a homograft malleus and tympanic membrane when the host malleus is absent, said prosthesis comprising an elongated lever member replacing the natural incus which collects sound from the tympanic membrane, said elongated lever member having first and second linear portions substantially at right angles to one another, and a third linear portion extending at an obtuse angle to said second linear portion at the end thereof remote from said first linear portion; means for attachment of one end of said lever member to the neck of the malleus at the axis of rotation of the malleus and the other end of said linear member to the manubrium of the malleus adjacent its umbo whereby to retain the natural cantilever effect of the tympanic membrane as a collecting lever of the manubrium; said means for attachment comprising a first U-shaped band secured to the free end of said first linear portion, and a second U-shaped band secured to the free end of said third linear portion, said first and second U-shaped bands lying in non-parallel planes; said first U-shaped band being deformable upon installation into a cylindrical configuration encircling the neck of the mallus at the axis of rotation of the malleus; said second U-shaped band being deformable upon installation into a cylindrical configuration encircling the manubrium of the malleus adjacent its umbo but out of contact with the tympanic membrane; said lever member and said U-shaped bands being fabricated from materials immune to resorption and host reaction.

3. The prosthesis of claim 2, wherein the inner surfaces of said first and second U-shaped bands are porous and have pore sizes ranging from about 50 to about 150 microns.

4. The prosthesis of claim 2, wherein said lever member and said U-shaped bands are fabricated from at least one of platinum, stainless steel, tantalum, titanium, and polytetrafluoroethylene.

5. The prosthesis of claim 3, wherein said porous inner surfaces are ceramic coatings.

6. The prosthesis of claim 3, wherein said porous inner surfaces are platinum.

7. The prosthesis of claim 2, including means for an adjustable connection to said second linear portion comprising a malleable U-shaped member adapted to be crimped around said second linear portion and fixedly laser welded thereto at a selected position, thereby providing a mechanical advantage ranging from 2:1 to 3:1, and a dependent inverted cup-like member having a concave porous inner surface adapted for ingrowth of bone thereinto, said concave inner surface begin configured to surround the capitulum of the stapes.

8. The prosthesis of claim 7, wherein said porous inner surface has pore sizes ranging from 50 to 150 microns.

9. The prosthesis of claim 2 for use in the middle ear when the stapes is absent, including a synthetic stapes, said synthetic stapes comprising a smooth-surfaced foot plate adapted to contact the oval window without fixation to its surrounding bony edges, an inverted U-shaped member the legs of which are secured to said foot plate, and a rod-like element secured to the top of said U-shaped member and projecting away from said foot plate, said rod-like element being attached to a malleable U-shaped member adapted to be crimped around said second linear portion and fixedly laser welded thereto at a selected position.

10. The prosthesis of claim 9, wherein said foot plate is fabricated from polytetrafluoroethylene, and said inverted U-shaped member, said rod-like element and said malleable U-shaped member are fabricated from at least one of platinum, stainless steel, tantalum, titanium and polytetrafluoroethylene.

* * * * *